(12) United States Patent
Fedida

(10) Patent No.: US 6,475,238 B1
(45) Date of Patent: *Nov. 5, 2002

(54) BIFURCATED AORTIC PROSTHESIS

(75) Inventor: José Fedida, Mouans-Sartoux (FR)

(73) Assignee: Novatech SA, Grasse le Plan (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/526,545

(22) Filed: Mar. 16, 2000

(30) Foreign Application Priority Data

Aug. 9, 1999 (FR) .............................. 99 10319

(51) Int. Cl.$^7$ ................................. A61F 2/06
(52) U.S. Cl. ...................................... 623/1.16
(58) Field of Search ................. 623/1.1, 1.11, 623/1.12, 1.13, 1.14, 1.15, 1.16, 1.17, 1.18, 1.19, 1.2, 1.21, 1.22; 606/108, 191, 194, 195, 198

(56) References Cited

U.S. PATENT DOCUMENTS 5,522,880 A * 6/1996 Barone et al. .............. 128/898
5,674,276 A * 10/1997 Andersen et al. ............ 623/1
5,683,449 A 11/1997 Marcade
5,693,088 A 12/1997 Lazarus
6,129,756 A * 10/2000 Kugler et al. .............. 623/1.27

FOREIGN PATENT DOCUMENTS

| EP | 0461791 A1 | 12/1991 |
| EP | 0880948 A1 | 12/1998 |
| FR | 2722678 A | 1/1996 |
| FR | 2775182 A | 8/1999 |
| WO | WO9521592 | 8/1995 |
| WO | WO9740779 | 11/1997 |
| WO | WO9806355 | 2/1998 |

* cited by examiner

Primary Examiner—Michael J. Milano
Assistant Examiner—Vy Q. Bui
(74) Attorney, Agent, or Firm—Steven, Davis, Miller & Mosher, LLP

(57) ABSTRACT

The present invention relates to a bifurcated aortic prosthesis comprising a structure (2) which comprises a main trunk (3) which divides into two branches (4, 5) of equal lengths and which has shape memory, and at least one impervious envelope (6) completely enveloping said branches (4, 5) and at least partially enveloping said trunk (3). According to the invention, said envelope (6) has a length (L) such that, in the position in which it is implanted in the aorta (AO), it approximately covers that part of the aorta (AO) which lies between the renal arteries (A1, A2) and the iliac arteries (A3, A4) and the length (l2) of said branches (4, 5) is between 1/4 and 2/5 of the length (L) of said envelope (6).

13 Claims, 2 Drawing Sheets

BIFURCATED AORTIC PROSTHESIS

Figure 1:
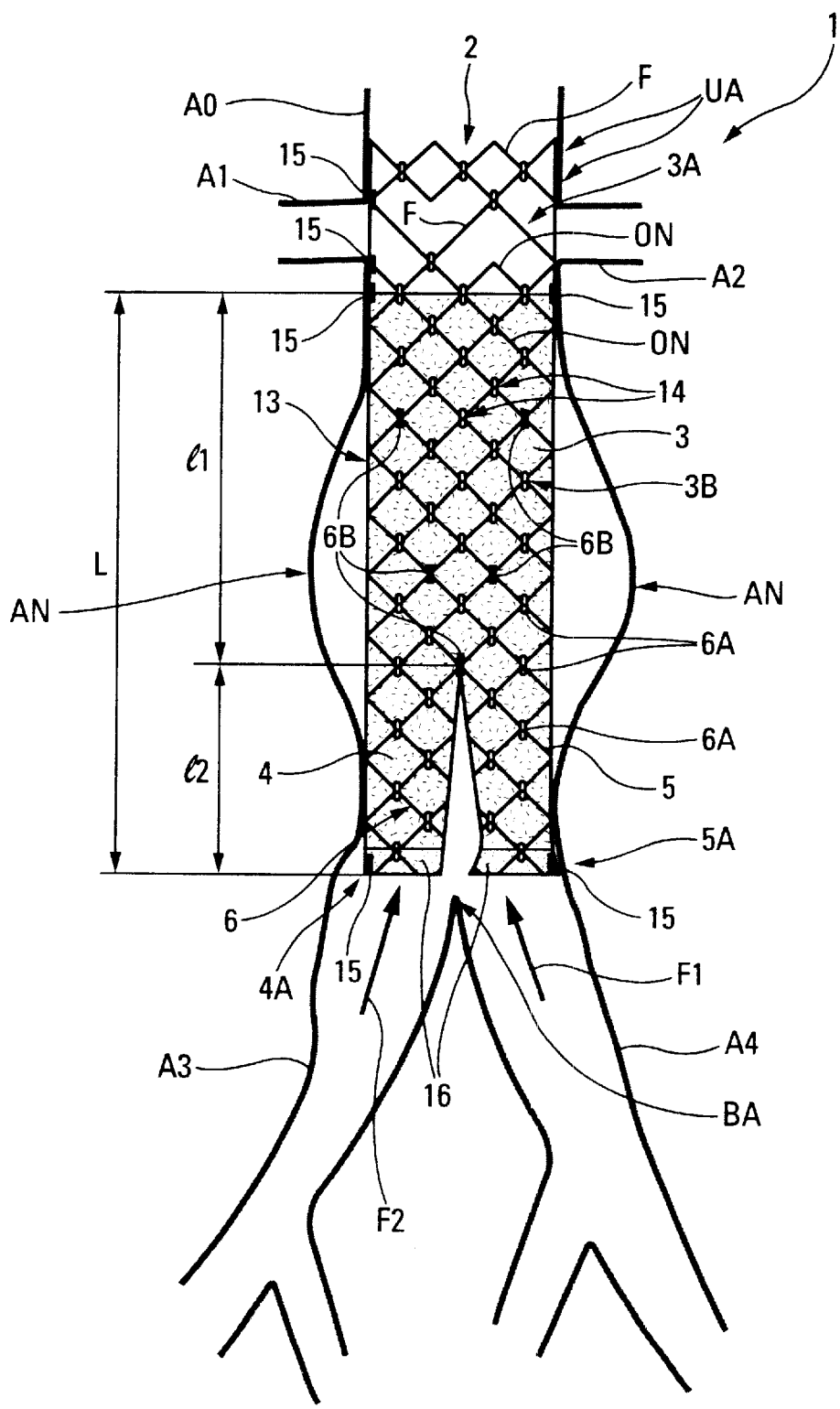

The present invention relates to a bifurcated aortic prosthesis.

This prosthesis is intended to be implanted in the abdominal aorta of a human body to treat an aneurysm of the aortic bifurcation, that is to say an aneurysm located on the abdominal aorta between the point where the renal arteries branch off and the fork of the iliac arteries, generally close to this fork.

Many examples of such prostheses are known. By way of illustration, mention is made of the documents WO-97/40779, WO-95/21592, EP-0 880 948 and EP-0 461 791.

Document WO-95/21592 in particular discloses a bifurcated aortic prosthesis comprising:

a structure which comprises a main trunk which divides into two branches of equal lengths, and which is produced in such a way as to allow said prosthesis to adopt one of two positions: a folded and compact position to allow the prosthesis to be implanted in said aorta and a position in which it is implanted and deployed in the aorta to create a substitute passage in the region of said aneurysm; and at least one impervious envelope at least partially enveloping said structure.

This prosthesis is small in size and is arranged near the renal arteries in such a way that it covers only a small part of the aneurysm. Two legs which just penetrate the iliac arteries are connected respectively to the said branches of the prosthesis. These legs thus cover the remainder of the aneurysm.

This embodiment has the drawback that the swirling flow of blood brought about by the aortic bifurcation (that is to say the fork at the iliac arteries) and which is generally responsible for the aneurysm moves upstream toward the renal arteries, something which is, of course, detrimental in the medium term and likely to cause a further aneurysm, in the vicinity of said renal arteries.

Furthermore, the structure of this prosthesis is such that it requires a significant amount of force to be generated in order to bring said prosthesis, when implanting it, from the folded position into the deployed position. This known document teaches the use of an inflatable balloon for generating such a force.

However, such use is difficult to perform and is also difficult to control. Furthermore, the inflating of the balloon completely cuts off the blood circulation, which makes it necessary to provide specific means or procedures for remedying the effects of a temporary interruption of the blood circulation.

Document EP-0 461 791 proposes, as an alternative to this implementation, a prosthesis which comprises a shape memory structure, which allows the structure to return automatically to the initial configuration, particularly the deployed configuration, without the use of specific means to achieve this.

The prosthesis described in that known document also differs from the one disclosed in document WO-95/21592 in that it has a far larger overall size, that is to say that both the trunk and the branches are larger, which means that the branches enter the iliac arteries over a relatively long distance. Furthermore, in a particular embodiment, the envelope completely covers said branches and partially covers said trunk. The envelope, which therefore penetrates the iliac arteries to a great extent, terminates at the other end well short of the renal arteries.

This known prosthesis has, as its major drawback, the fact that it is particularly tricky to fit and that this fitting requires a lengthy and complex procedure. This is because, in this case, the prosthesis is first of all brought from a femoral artery via an iliac artery into the aorta at the region of the aortic bifurcation and therefore the region of the aneurysm. For this purpose, the two branches of the prosthesis are continuous and introduced into one and the same delivery device. After the latter has been withdrawn, the two branches are located in one and the same iliac artery and one of said branches therefore has to be extracted from this iliac artery and led across into the other iliac artery.

This prosthesis is therefore particularly tricky and lengthy to fit.

The object of the present invention is to overcome these drawbacks. The invention relates to a bifurcated aortic prosthesis intended to be implanted in the aorta of a human body to treat an aneurysm of the aortic bifurcation, which prosthesis can be implanted simply and quickly, which allows effective treatment of the aneurysm and in addition prevents the aforementioned swirling flow of blood from moving back upstream toward the renal arteries.

To this end, said prosthesis, of the known type described, in particular, in document EP-0 461 791, and comprising:

a structure which comprises a main trunk which divides into two branches of equal lengths, which is of the shape memory type and which is produced in such a way as to allow said prosthesis to adopt one of two positions: a folded and compact position to allow the prosthesis to be implanted in said aorta and a position in which it is implanted and deployed in the aorta to create a substitute passage in the region of said aneurysm; and at least one impervious envelope completely enveloping said branches and at least partially enveloping said trunk, is noteworthy, according to the invention, in that said envelope has a length such that, in said implanted position, it approximately covers that part of the aorta which lies between the renal arteries and the iliac arteries and in that the length of said branches is between ¼ and ⅖ and is preferably close to ⅓ of the length of said envelope.

Thus, by virtue of the invention:

as the branches of the structure which are completely covered by the envelope do not enter the iliac arteries, the prosthesis is simpler and easier to fit, particularly by comparison with the aforementioned solution recommended by document EP-0 461 791. Furthermore, the length of said branches, although short, is long enough to allow a good grip and therefore, in particular, to allow additional legs to be assembled easily with the free ends of said branches. The fitting of the prosthesis is, of course, made easier by the use of a structure with shape memory;

since the entire region between the iliac arteries and the renal arteries is covered by the envelope, the entire aneurysm is treated (by the substitute passage created by the prosthesis). Of course, said envelope is made of a biocompatible material which, while being impervious to the flow of blood, remains permeable to cellular exchanges; and since that part of the trunk which is covered by the envelope is very long (between ⅗ and ¾ of the distance between the iliac aortas and the renal arteries), the swirling flow of blood caused by the aortic bifurcation is calmed at least greatly, if not completely, in this covered part and does not therefore travel back upstream toward the renal arteries.

According to the invention, the diameter of said branches is approximately equal to half the diameter of said main trunk. In consequence, the diameter of the branches is greater than in the aforementioned known prostheses, and this makes it possible to improve the flow of blood at the point where the branches connect to the trunk of the prosthesis.

Advantageously, at least one of said branches is flared at its free end, which makes it easier to attach an additional leg implanted in one of the iliac arteries.

Furthermore, advantageously, at the free end of at least one of said branches said envelope has a turned-back region, which allows it to seal with the additional leg assembled to said branch.

What is more, to fix the envelope to the structure in a robust and durable way, said envelope is sewn at least at its opposite end to the free end of the branches.

Furthermore, advantageously, the prosthesis according to the invention comprises at least one radio-opaque element, which allows the prosthesis to be readily detected and precisely pinpointed in the human body by radiography while it is being implanted and/or after it has been implanted. The radio-opaque element or elements used, for example known elements attached in a specific way, or preferably the linking means described hereinbelow, may be provided at various points on the structure. Advantageously, the prosthesis according to the present invention comprises:

at least one radio-opaque element arranged at the free end of at least one of said branches; and/or
  at least two radio-opaque elements arranged on said structure in such a way as, in the implanted position, to delimit the branch connection of at least one of the renal arteries; and/or
  a number of radio-opaque elements arranged in a V-shape and connecting the fork between the two branches, on the two sides of the trunk respectively, to the opposite end of the envelope to the branches.

In one preferred embodiment, said structure is at least partially produced in the form of a mesh and has at least one corrugated filament forming approximately annular units linked together. At least some of the corrugations of said corrugated filament of two adjacent units respectively are linked to one another by linking means. At least some of said linking means comprise links which are made as a rigid piece and provided with at least two loops joined together; and, in the case of each of said links, each of the two loops of said link entraps, with some clearance, a respective one of the two corrugations that are to be linked.

In the context of the present invention, some of the links may be radio-opaque and used as radio-opaque elements for allowing the detection of the prosthesis.

The figures of the appended drawing will make it easy to understand how the invention may be embodied. In these figures, identical references denote similar elements.

FIG. 1 diagrammatically illustrates a bifurcated aortic prosthesis according to the invention.

Figure 2:
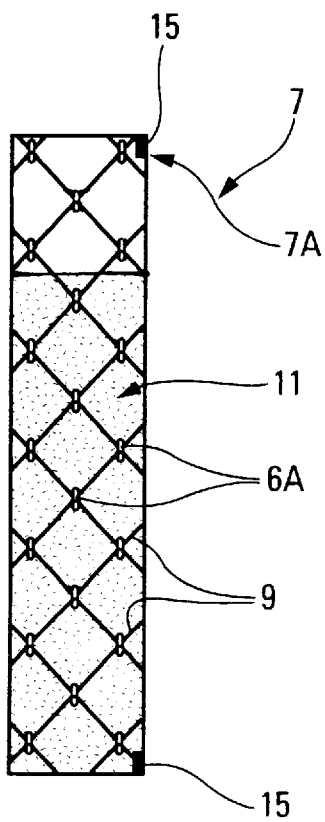
Figure 3:
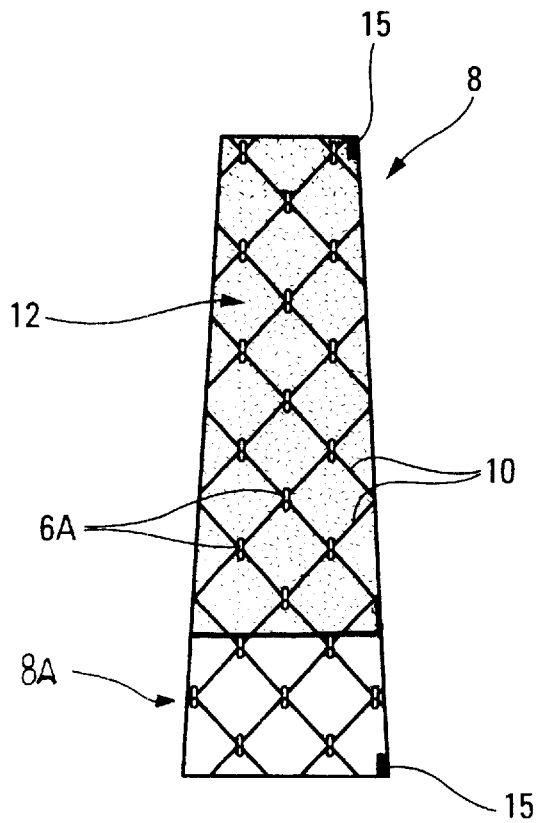

FIGS. 2 and 3 diagrammatically show legs, in two different embodiments respectively, which legs can be secured to the branches of the prosthesis of FIG. 1.

Figure 4:
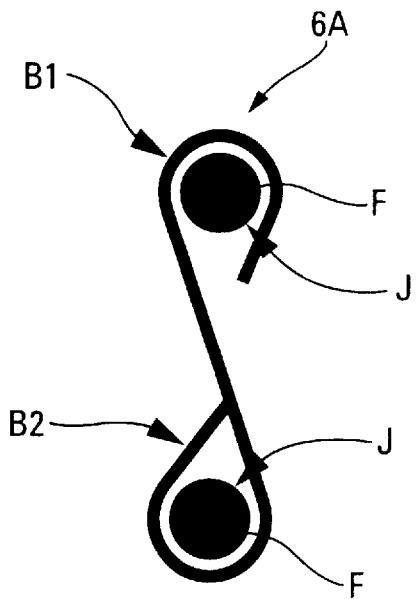
Figure 5:
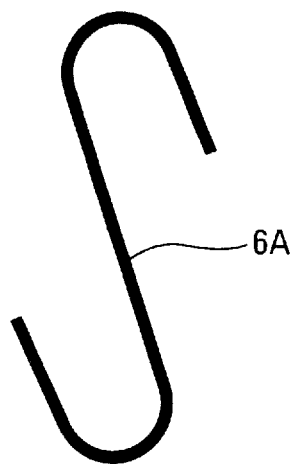

FIGS. 4 and 5 diagrammatically illustrate preferred linking means for the structure of the prosthesis depicted in FIG. 1, in opened and closed positions respectively.

The bifurcated aortic prosthesis 1 according to the invention and depicted diagrammatically in FIG. 1 is intended to be implanted in the abdominal aorta AO of a human body to treat an aneurysm of the aortic bifurcation BA, that is to say an aneurysm AN located on the abdominal aorta AO between the point where the renal arteries Al and A2 branch off and the fork BA of the iliac arteries A3 and A4.

In the known way, said prosthesis 1 comprises:

a structure 2 which comprises a main trunk 3 which divides into two branches 4, 5 and which is produced in such a way as to allow said prosthesis to adopt one of the two following positions: a folded and compact position to allow the prosthesis 1 to be implanted in said abdominal aorta AO and a position in which it is implanted and deployed in the aorta AO, as depicted in FIG. 1, to create a substitute passage in the region of said aneurysm AN; and
  an impervious envelope 6, for example made of polyester textile, which partly covers said structure 2. Of course, said envelope 6 must be made of a biocompatible material which, while being impervious to the flow of blood, remains permeable to cellular exchanges.

In particular, to make the prosthesis 1 easier to implant, the structure 2 is a structure with shape memory, which allows the prosthesis 1 which is initially in the deployed position and which is forced into the folded position for being implanted, to return automatically to said deployed position once it has been introduced into the aorta AO as depicted in FIG. 1. No specific means such as an inflatable balloon is therefore needed to bring the prosthesis 1 into the functional (deployed) position.

According to the invention and as can be seen in FIG. 1:

the impervious envelope 6 completely envelopes the two legs 4 and 5 and partially envelopes the trunk 3 (over a length l1) so that it approximately covers that part of the aorta Al which lies between the renal arteries Al and A2 and the iliac arteries A3, A4; and
  the length 12 of said branches 4 and 5 is between ¼ and ⅖, and is preferably close to ⅓, of the length L of said envelope 6.

In general, although not exclusively:

the length l1 is of the order of 7 to 8 cm; and
  the length 12 is of the order of 4 to 5 cm.

Thus, by virtue of the invention:

as the branches 4, 5 (of equal length) of the structure 2 which are completely covered by the envelope 6 do not enter the iliac arteries A3, A4, the prosthesis 1 is simpler and easier to fit. This fitting is of course made easier by the use of a structure with shape memory;
  as the entire region between the iliac arteries A3, A4 and the renal arteries A1, A2 is covered, the entire aneurysm AN is treated (by the substitute passage created by the prosthesis 1); and
  since that part 3B of the trunk 3 which is covered by the envelope 6, is of very long length l1 (between ⅗ and ¾ of the distance, approximately equal to L, between the iliac arteries A3, A4 and the renal arteries A1, A2), the swirling flow of blood caused by the aortic bifurcation is greatly or even completely calmed in this covered part 3B and does not therefore travel back upstream toward the renal arteries A1, A2.

It will be noted that, according to the invention, the branches 4 and 5 also have a "large" diameter, for example of the order of 12 to 14 mm, which is preferably approximately equal to half the diameter of the trunk 3, thus encouraging good flow of blood between said trunk 3 and said branches 4 and 5.

What is more, the length 12 of the branches 4 and 5, which is an "average" length, allows legs 7, 8 to be fitted easily to the free ends 4A, 5A thereof, as illustrated in FIG. 1 by arrows F2 and F1 which represent the direction in which such legs 7, 8 are fitted.

These legs 7, 8 each comprise, as depicted in FIGS. 2 and 3:

a structure 9, 10, preferably of the same type as the structure 2 of the prosthesis 1, which, for example, has a cylindrical shape like the structure 9 depicted in FIG. 2, or a frustoconical shape like the structure 10 depicted in FIG. 3; and an impervious envelope 11, 12, preferably of the same type as the envelope 6 of the prosthesis 1, which covers said structure 9, 10 except for a small part, for example 1 centimeter long, at the end 7A, 8A which is intended to be joined to one of said branches 4, 5 of the prosthesis 1. As can be seen, the relative orientations of the legs 7 and 8 of FIGS. 2 and 3 are reversed.

To make such joining easier, the branch 5 is flared at its free end 5A.

It will be noted that a feature such as this (flared end) is not necessarily needed for the placement of one of said branches of the prosthesis 1, in this instance the branch 4, because this placement generally uses a known guide used previously for fitting the prosthesis 1, which means that the guidance of the associated leg is generally very accurate and sufficient. However, the branch 4 may of course also be flared at its free end 4A.

Furthermore, according to the invention, the envelope 6 has a turned-back region 16 at the region of the branches 4, 5, and this in particular allows for good imperviousness of the assembly formed by the prosthesis 1 and the legs, after the latter have been fitted.

In addition, to obtain a robust attachment of the envelope 6 to the structure 2, said envelope 6 is sewn at least at its ends.

As indicated previously, the trunk 3 of the structure 2 has a part 3B covered by the envelope 6 and a part 3A which is uncovered. According to the invention, said part 3A, which extends up beyond the renal arteries A1, A2, allows the prosthesis 1 to be fixed easily to a healthy part of the aorta AO in the region of said renal arteries A1 and A2.

Furthermore, as can be seen in FIG. 1, said structure 2 in the region where the renal arteries A1 and A2 branch off, has a widened mesh structure so that it does not hamper or disrupt the flow of blood between the aorta AO and said renal arteries A1 and A2.

In the context of the present invention, the structure 2 of the prosthesis 1 may be in various known forms.

As a preference, however, said structure 2 comprises, in the known way, at least one mesh 13 which is at least partially cylindrical and which comprises at least one corrugated filament F forming approximately annular corrugated units UA linked together. These annular corrugated units UA have a number of corrugations ON. In addition, at least some of these corrugations ON, each time belonging to two adjacent units UA, are linked together by linking means 14, so as to connect said adjacent annular units UA together and thus form said cylindrical mesh 13.

In the context of the present invention, each annular unit UA may be made of a specific filament F, so that the various annular units UA are then completely independent of one another before they are linked together.

However, it is equally possible to produce the collection of annular units UA using one and the same filament F. For this purpose, the filament F is configured so that, having created an annular unit UA, it passes on to the next annular unit UA.

According to the invention, particularly to allow a robust, flexible durable connection not injuriant to the aorta AO, at least some of the linking means 14 comprise special-purpose links 6A, 6B described hereinbelow.

According to the invention, such a link 6A, 6B is made of a rigid piece and comprises, as depicted in FIGS. 4 and 5 in the case of the link 6A, at least two loops B1 and B2, each of which entraps, with a certain clearance J, one of the corrugations or parts of the filament F that are to be linked together. The loops B1 and B2 are such that the parts of filament (entrapped with clearance) while being secured firmly together are able to move (turn) freely, which makes it possible to achieve a link which has the aforementioned characteristics.

Specifically:

the link is robust and durable, by virtue of the rigidity of the link 6A and the fact that loops B1 and B2 are generated in the actual part of the link 6A;

the linked connection is very flexible, particularly by virtue of the clearance J and the separation between the two parts of filament F which are to be linked together; and the linked connection does not, for example, have any projecting parts and there is therefore no danger that it will harm the wall of the aorta AO in which the prosthesis 1 is implanted.

It will be noted that FIG. 4 illustrates a closed or linking position of the link 6A and that FIG. 5 illustrates the open position of this link 6A prior to linking.

In the context of the present invention:

the filament F and the links 6A may be made of metal or, for example, of a known material marketed under the name of "nitinol";

the loops, such as the loop B2 in FIG. 4, may be completely closed, thus affording an extremely robust connection;

said links may also be just partially closed, that is to say closed just enough to effectively entrap that part of the filament or corrugation that is to be linked, as is the case of loop B1 in FIG. 4, which of course makes the loops easier to produce.

It will be noted that the part 3A of the trunk 3 of said structure 2 comprises, for example, a single annular unit UA downstream of the renal arteries A1, A2 and two annular units UA upstream of these. Furthermore, the annular unit located directly in the region of said renal arteries A1, A2 has corrugations which are stretched out so as not to disrupt or block the flow of blood between the aorta AO and these renal arteries A, A2.

Furthermore, to make the prosthesis 1 easy to detect and precisely pinpoint while it is being implanted in the aorta AO or after this implantation, said prosthesis 1 has radio-opaque elements 6B, 15. The same is true of the legs 7 and 8, as depicted in FIGS. 2 and 3.

As far as these radio-opaque elements are concerned, these may be;

either conventional radio-opaque elements 15 attached in a specific way;

or links 6B which have the same shape as the links 6A described hereinabove, these links 6B also being made radio-opaque by the use of an appropriate material or coating.

As can be seen in FIG. 1, the prosthesis 1 comprises:

one radio-opaque element 15 at the end of each of the branches 4 and 5;

two radio-opaque elements 15 which, in the implanted position, delimit one A1 of the renal arteries; and a number of radio-opaque elements 6B, 15 arranged in a V-shape and connecting the fork between the two branches 4 and 5 on the two sides of the trunk 3 respectively, to the opposite end of the envelope 6 to the branches 4 and 5.

What is claimed is:

1. A bifurcated aortic prosthesis intended to be implanted in the abdominal aorta of a human body to treat an aneurysm of the aortic bifurcation, said prosthesis comprising:

a single-piece structure which comprises a main trunk which divides into two branches of equal lengths, which is of the shape memory type and which is produced in such a way as to allow said prosthesis to adopt one of two positions: a folded and compact position to allow the prosthesis to be implanted in said aorta and a position in which the prosthesis is implanted and deployed in the aorta to create a substitute passage in the region of said aneurysms; and at least one impervious envelope completely enveloping said branches and at least partially enveloping said trunk, wherein said envelope has a length such that, in said implanted position, said envelope approximately covers that part of the aorta which lies between the renal arteries and the iliac arteries and a length of said branches is between ¼ and ⅖ of the length of said envelope.

2. The prosthesis as claimed in claim 1, wherein the length of the branches represents approximately ⅓ of the length of the envelope.

3. The prosthesis as claimed in claim 1, wherein the diameter of said branches is approximately equal to half the diameter of said main trunk.

4. The prosthesis as claimed in claim 1, wherein at least one of said branches is flared at its free end.

5. The prosthesis as claimed in claim 1, wherein, at the free end of said at least one of said branches said envelope has a turned-back region.

6. The prosthesis as claimed in claim 1, wherein said envelope is sewn at least at its opposite end to the free end of said at least one of said branches.

7. The prosthesis as claimed in claim 1, further comprising at least one radio-opaque element.

8. The prosthesis as claimed in claim 7, further comprising at least one radio-opaque element arranged at the free end of said at least one of said branches.

9. The prosthesis as claimed in claim 7, further comprising at least two radio-opaque elements arranged on said structure in such a way as, in the implanted position, to delimit the branch connection of at least one of the renal arteries.

10. The prosthesis as claimed in claim 7, further comprising a number of radio-opaque elements arranged in a V-shape and connecting the fork between the two branches, on the two sides of the trunk respectively, to the opposite end of the envelope to the branches.

11. The prosthesis as claimed in claim 1, wherein said structure has an end part which is not covered by the envelope and which is intended for fixing the structure to the aorta in the region of the renal arteries.

12. The prosthesis as claimed in claim 1, wherein said structure is at least partially produced in the form of a mesh and has at least one corrugated filament forming approximately annular units linked together, at least some of the corrugations of said corrugated filament of two adjacent units respectively are linked to one another by linking means; at least some of said linking means comprise links which are made as a rigid piece and provided with at least two loops joined together; and, in the case of each of said links, each of the two loops of said link entraps, with some clearance, a respective one of the two corrugations that are to be linked.

13. The prosthesis as claimed in claim 12, wherein at least one of said links is radio-opaque.

* * * * *